United States Patent [19]

Share

[11] Patent Number: 5,922,820
[45] Date of Patent: Jul. 13, 1999

[54] POLYMERIZABLE COMPOUNDS

[75] Inventor: Paul E. Share, Moon Township, Pa.

[73] Assignee: Henkel Corporation, Gulph Mills, Pa.

[21] Appl. No.: 08/577,654

[22] Filed: Dec. 22, 1995

Related U.S. Application Data

[63] Continuation-in-part of application No. 08/242,797, May 19, 1994, Pat. No. 5,565,567, which is a continuation-in-part of application No. 08/073,014, Jun. 4, 1993, abandoned.

[51] Int. Cl.⁶ .................................................. C08L 39/04
[52] U.S. Cl. .......................... 526/258; 544/386; 544/406
[58] Field of Search ............................ 526/258; 544/386, 544/406

[56] References Cited

U.S. PATENT DOCUMENTS

| | | | |
|---|---|---|---|
| Re. 29,131 | 2/1977 | Smith et al. ........................... | 260/77.5 |
| 3,352,866 | 11/1967 | Dornfeld .................................. | 544/386 |
| 3,510,247 | 5/1970 | Tesoro et al. ............................ | 8/116.2 |
| 3,528,964 | 9/1970 | Tesoro ..................................... | 260/231 |
| 3,935,330 | 1/1976 | Smith et al. .............................. | 427/41 |
| 4,215,195 | 7/1980 | Ponticello et al. ...................... | 430/496 |
| 4,220,646 | 9/1980 | Cortrel et al. ........................... | 544/373 |
| 4,247,673 | 1/1981 | Ponticello et al. ...................... | 526/263 |
| 4,346,231 | 8/1982 | Ponticello et al. ...................... | 560/178 |
| 4,940,793 | 7/1990 | Botre et al. .............................. | 544/386 |
| 5,045,427 | 9/1991 | Hara ........................................ | 430/138 |
| 5,138,027 | 8/1992 | Van Beek ................................ | 528/339 |
| 5,192,766 | 3/1993 | Nakamura et al. ...................... | 514/255 |
| 5,565,567 | 10/1996 | Share ....................................... | 544/295 |
| 5,708,107 | 1/1998 | Ahmed et al. ........................... | 526/263 |

FOREIGN PATENT DOCUMENTS

| | | |
|---|---|---|
| 053047 | 6/1982 | European Pat. Off. . |
| 0356960 | 3/1990 | European Pat. Off. . |
| 0519297 | 12/1992 | European Pat. Off. . |
| WO9429296 | 12/1994 | WIPO . |

OTHER PUBLICATIONS

Body et al., "1,2–Epoxide Polymers", *Encyclopedia of Polymer Science and Engineering*, vol. 6, pp. 223–322 (John Wiley & Sons, New York, New York 1986).

*Encyclopedia of P. Science & Engineering*, vol. 11, pp. 476–489 (John Wiley & Sons, Inc., NY, NY 1988).

R. Larock, *Comprehensive Organic Transformations: A Guide to Functional Group Preparations*, pp. 978 and 979 (VCH Publisher, NY, NY 1989).

Chemical and Pharmaceutical Bulletin, issued 1984, Shiozawa et al., "Antivertigo Agents. IV. Synthesis and Antivertigo Activity of 6–[w–(4–Aryl–1–piperazinyl) alkyl]–5,6,7,8,–tetrahydro–1,6–naphthyridines", pp. 3981–3993.

M. Taningher et al., "Genotoxicity of N–acryloyo–N'–phenylpiperazine, a Redox Activator for Acrylic Resin Polymerization," *Mutation Research*, vol. 282, pp. 99–105 (1992).

*Encyclopedia of Polymer Science and Engineering*, vol. 3, pp. 552–675; John Wiley & Sons, New York.

Thomas et al., Acrylate Polymers, *Encyclopedia of Polymer Science and Engineering*, vol. 1, 169–211; John Wiley & Sons, New York.

*Encyclopedia of Polymer Science and Engineering*, supp. vol. pp. 53, 109, 110, John Wiley & Sons, New York.

*Encyclopedia of Chemical Technology*, vol. 2, pp. 252–258; vol. 2, pp. 67, 68 and pp. 795, 803–806; vol. 12, pp. 319–321; vol. 9, pp. 306–308; John Wiley & Sons, New York.

E.J. Murphy et al., "Some Characteristics of Steric Polymerization", Proceedings of Rad Tech 1990—North America, vol. 1, pp. 217–226.

*Primary Examiner*—Bernard Lipman
*Attorney, Agent, or Firm*—Wayne C. Jaeschke; Glenn E.J. Murphy; Daniel S. Ortiz

[57] ABSTRACT

Polymerizable compositions containing compounds based on N-acylamido-piperazines are provided. Such compounds have the formula:

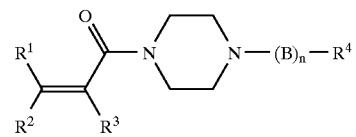

wherein:

$R^1$, $R^2$, and $R^3$ are each independently selected from the group consisting of hydrogen and lower alkyl, B is a linking group selected from the group consisting of carbonyl, sulfonyl, amide, and carboxyl;

n is one or zero;

$R^4$ is a radical selected from the group consisting of a higher aliphatic group (i.e. at least four carbon atoms, preferably from about 6 to about 50 carbon atoms), a substituted higher aliphatic group, an alicyclic group, a heterocyclic group, a non-benzenoid aromatic group, and a substituted aromatic group. Compositions containing these compounds which are stable against gelation can be prepared. The compound is preferably present in said composition in a major amount on a mole percent basis of the polymerizable monomers. These polymerizable compositions are useful as coatings, particularly in formulations containing a photoinitiator susceptible to ultra-violet radiation. The coating is exposed to ultra-violet radiation sufficient to cause the compound to polymerize and thus cure the coating.

38 Claims, No Drawings

POLYMERIZABLE COMPOUNDS

RELATED U.S APPLICATION DATA

This application is a continuation-in-part of U.S. Ser. No. 08/242,797 filed May 19, 1994, now U.S. Pat. No. 5,565,567 which is a continuation-in-part of U.S. Ser. No. 08/073,014, Jun. 4, 1993, abandoned.

FIELD OF THE INVENTION

The present invention relates to polymerizable compounds and to their use. More particularly, it relates to N,N'-substituted piperazine acrylamide compounds and to processes of polymerizing these compounds, e.g. for preparing coatings.

BACKGROUND OF THE INVENTION

The use of N,N'-substituted piperazine is disclosed in a number of documents. U.S. Pat. No. 5,192,766 purports to disclose N-acryloylpiperazine derivatives and their pharmaceutical use as platelet activating factor antagonists. While the title uses the term N-acryloylpiperazine, it is clear from the disclosure that the compounds disclosed have a phenyl substituent bonded to the alpha,beta-unsaturated acylamido group such that the compounds are, thus, apparently cinnamoyl derivatives or homologues thereof.

M. Taningher et al., "Genotoxicity of N-acryloyl-N'-phenylpiperazine, a Redox Activator for Acrylic Resin Polymerization", *Mutation Research*, vol. 282, pp. 99–105 (1992) discusses the use of N-acryloyl-N'-phenylpiperazine as a promoter of redox reactions in place of other tertiary aromatic amines, e.g. N,N-dimethylaniline. It is speculated that the acryloyl group will allow the compound to be copolymerized into the final material and thus avoid release thereof into the environment.

U.S. Pat. No. 5,045,427 discloses the use of a variety of polymerizable compounds, including N,N'-bis-acrylamido-piperazine, in a photographic material. This photographic material is comprised of a support on which is provided a light-sensitive layer comprised of a photosensitive silver halide, a non-photo-sensitive silver salt, a reducing agent, a color image-forming material and a polymerizable compound.

EP-0356960 discloses polyacrylamide gels which employ as crosslinking agents diacylyl compounds with tertiary amide groups, e.g. diacrylyl piperazine (a.k.a. N,N'-bis-acrylamido-piperazine). These gels contain a chaotropic agent which permits the use of the gels in the separation of proteins or nucleic acids.

U.S. Pat. No. 3,510,247 discloses the modification of cellulosic materials with tertiary bis-acrylamides, e.g. diacryloyl piperazine (a.k.a. N,N'-bis-acrylamido-piperazine). The bis-acrylamide is applied to the cellulosic substrate and a crosslinking reaction is catalyzed by the use of an alkaline compound and elevated temperatures, generally 200 degrees F to 350 degrees F. U.S. Pat. No. 3,528,964 discloses a similar modification, but the amides are sulfonic acid amides, wherein the sulfonic acid groups contain ethylenic unsaturation.

The technology for the production of coatings by curing monomeric compositions on the surface of various substrates is generally known. For example, J. Lowell, "Coatings", *Encyclopedia of Polymer Science and Engineering*, vol.3, pp. 615–675, discusses, at page 647, the production of coatings by free-radical polymerization of monomers, e.g. unsaturated polyesters in a solution of an unsaturated monomer such as styrene, acrylates, and methacrylates, and polyfunctional low volatility monomers such as trimethylolpropane triacrylate. When such systems are cured with ultra-violet radiation, a photoinitiator such as benzophenone is often used to increase the production of free-radicals and thereby promote curing of the coating.

While N,N'-bis-acrylamido-piperazine is a useful monomer in many applications, it has been found its performance as the major component of a radiation curable composition has certain drawbacks. For example, it has been observed that cured films thereof are quite brittle.

SUMMARY OF THE INVENTION

This invention relates to a composition of matter comprising a compound of the formula I:

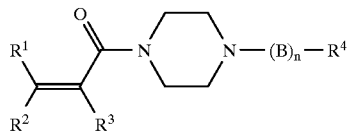

wherein:

$R^1$, $R^2$, and $R^3$ are each independently selected from the group consisting of hydrogen and lower alkyl (preferably $R^1$ and $R^2$ are hydrogen and $R^3$ is hydrogen or methyl), B is a linking group selected from the group consisting of carbonyl, sulfonyl, amide, and carboxyl;

n is one or zero;

$R^4$ is a radical selected from the group consisting of a higher aliphatic group (i.e. at least three carbon atoms, preferably from about 4 to about 50 carbon atoms and more preferably about 7 to about 50 carbon atoms), a substituted higher aliphatic group, an alicyclic group, a heterocyclic group, a non-benzenoid aromatic group, and a substituted aromatic group (said substituted aromatic group preferably having an aliphatic group or a substituted aliphatic group as substituents, e.g. an alkyl group, an alkaryl group, an aralkyl group, an alkoxy group, an alkaryloxy group, an aralkoxy group, an acyl group or a carboalkoxy group (e.g. —C—(O)—O-alkyl), preferably each having at least four carbon atoms), wherein said composition is stable against gelation, i.e. does not gel (e.g. set to a solid mass) after an extended period of time, e.g. at least about 150 hours, at an elevated temperature, e.g. about 60° C. It has been found that compositions which contain compounds of the above formula may contain sufficient concentrations of residual free amine compounds to cause the composition to gel when maintained at elevated temperatures for extended periods of time. Compositions which have been produced in such a way as to avoid the presence of such concentrations have been found to exhibit improved high temperature stability.

A preferred class of compositions contain compounds within the scope of this invention having the formula II:

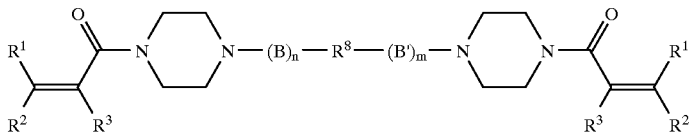

wherein each $R^1$, $R^2$ and $R^3$ is independently selected from the group consisting and lower alkyl, each B and B' linking group is independently selected from the group consisting of carbonyl, sulfonyl, amide, and carboxyl;

n and m are independently one or zero;

$R^8$ is a divalent radical selected from the group consisting of an aliphatic group, an alicyclic group, an aromatic group, and a heterocyclic group (preferably a higher alkylene group (i.e. at least four carbon atoms, preferably from about 5 to about 50 carbon atoms), a substituted higher alkylene group, an aryl group (preferably a phenyl group), an aralkyl group, and an alkaryl group.

Another special class of compounds within the scope of this invention have the following formula III:

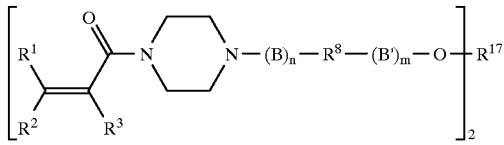

wherein the variables have the same meaning as set forth above and $R^{17}$ is a polyvalent radical selected from the group consisting of an aliphatic group, an alicyclic group, an aromatic group, and a heterocyclic group (preferably an alkylene group, a substituted alkylene group, an aralkyl group, a substituted aralkyl group, an alkyleneoxyalkyl group, a substituted alkyleneoxyalkyl group, an alkyleneoxyaralkyl group, a substituted alkyleneoxyaralkyl group).

Particularly preferred compounds of this invention are those wherein n is one (and B is preferably a carbonyl group) and $R^4$ is an alkylene-amido group having the structure —$R^8$—C(O)—N($R^9$)—$R^{10}$ or an alkylene-ester group having the structure —$R^8$—C(O)—O—$R^{11}$, wherein $R^8$ is a divalent group selected from the group consisting of a higher alkylene group, a substituted higher alkylene group, an aromatic group, and a substituted aromatic group, and $R^9$, $R^{10}$, and $R^{11}$ are independently selected from the group consisting of an aliphatic group, an alicyclic group, an aromatic group, and a heterocyclic group (preferably an alkyl group, a substituted alkyl group, an alkenyl group, a substituted alkenyl group, an aromatic group, and a substituted aromatic group), provided that $R^9$ and $R^{10}$ may together form a divalent alicyclic or heterocyclic radical, e.g. wherein $R^4$ has the formula IV:

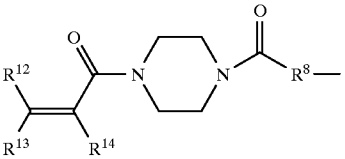

wherein $R^{12}$, $R^{13}$, and $R^{14}$ are independently selected from the group consisting of hydrogen and lower alkyl.

This invention also relates to a polymerizable composition comprising a composition comprising a compound of formula I, above, and to a method of coating a substrate comprising (i) contacting a surface of a substrate with a polymerizable composition comprising a compound of formula I, above, and (ii) exposing said surface to radiation sufficient to cause said compound to polymerize in contact with said surface. In preferred methods, said compound is present in said composition in a major amount on a mole percent basis of all of the monomers of said polymerizable composition.

DETAILED DESCRIPTION OF THE INVENTION

This invention relates to novel compositions of this invention, e.g. compositions containing compounds of formula I, and to methods of making these novel compositions. These compounds are piperazine derivatives in which one of the amine nitrogen atoms of the piperazine molecule has been reacted with an acylating agent to introduce the acrylamido group (or a homologue thereof) which contains the groups $R^1$, $R^2$, and $R^3$, and in which the other piperazine nitrogen atom has been reacted with a compound to introduce the $R^4$ group (and optionally a B linking group) into the molecule. Thus, one of the starting materials for preparing the novel compounds of this invention is piperazine, or a derivative thereof (e.g. an amide that is susceptible to trans-amidation).

Because piperazine has secondary amine groups, there is a possibility that compositions prepared therefrom will contain residual free secondary amine, e.g. from unreacted piperazine or a piperazinyl-functional intermediate. It is believed that the presence of even small amounts of such impurities can lead to gelation of compositions which contain compounds of formula I. Such gelation is believed to be caused by reaction of the residual free secondary amine with the ethylenic unsaturation of the compounds of formula I.

The composition of the invention should not gel when held at a temperature of 60° C. for an extended period of time, preferably at least about 150 hours, more preferably at least about 175 hours, and even more preferably at least about 200 hours. The compositions of this invention will typically not gel after at least 300 hours at 60° C. and most preferably at least about 450 hours.

A means of evaluating the stability of the compositions of this invention with respect to gelation is to subject the composition to heat aging and to measure the viscosity of the aged composition. For example, the viscosity of the composition is measured, e.g. at an ambient temperature of 25° C. Then, the composition is aged by placing it in an oven at 60° C. After aging and cooling to an ambient temperature of 25° C., the viscosity of the composition is then measured again. If there is a significant increase in the viscosity of the composition after such aging, the composition thus shows a tendency to gel. Preferably, the composition will show an increase in viscosity of less than 100%, more preferably less than 50%, and even more preferably less than 20%, after a period at 60° C. of at least about 3 hours, more preferably, at least about 24 hours and even more preferably at least about 150 hours. Ideally, the composition will show no increase in viscosity that is measurable within the limits of detection of the apparatus and procedure chosen after being held for more than 150 hours at 60° C. An example of a useful viscometer is a cone and plate viscometer available as the Carri-Med CSL Rheometer, distributed by Mitech Corp., Twinsburg, Ohio, and manufactured by Carri-Med Ltd., Dorking, Surrey, UK.

Because of the presence of free secondary amine groups which is thought to cause gelation of compositions containing compounds of this invention, it is believed that methods of making the compositions of this invention which minimize the presence of residual free secondary amine will be useful in preparing compositions of this invention. Such methods include the use of a catalyst, as discussed more fully below, for the reactions which consume the free secondary amine functionality of the piperazine starting material and/or piperazinyl intermediate.

Also, techniques to reduce the reactivity of the mixture, such as the inclusion of polymerization inhibitors in the composition. A preferred polymerization inhibitor in this regard is phenothiazine. Quinones, e.g. methyl hydroquinone is also useful as an inhibitor, but the mechanism of inhibition of quinones such as methyl hydroquinone requires the presence of oxygen for effective inhibition and it may not be practical to maintain sufficient levels of oxygen in the compositions to allow the use of such inhibitors.

The group $R^4$ is an aliphatic, substituted aliphatic, non-benzenoid aromatic, or substituted aromatic radical having at least four carbon atoms, preferably from 4 to about 50 carbon atoms. Such aliphatic radicals include any (a) straight chain and branched alkyl radicals having from 4 to about 50 carbon atoms; (b) cycloalkyl radicals having from 4 to about 20 carbon atoms; (c) straight chain and branched alkenyl radicals having from 4 to about 40 carbon atoms; (d) cycloalkenyl radicals having from 5 to about 20 carbon atoms; (e) straight chain and branched alkynyl radicals having from 4 to about 30 carbon atoms; cycloalkynyl radicals having from 6 to about 20 carbon atoms. Aliphatic radicals also include those above-mentioned aliphatic radicals which contain one or more heteroatoms substituted for one or more hydrogen or carbon atoms. The heteroatoms include the halogens, nitrogen, sulfur, oxygen, and phosphorus or groups of heteroatoms such as nitro, sulfonic acid, $C_{1-10}$ alkyl sulfonate ester, sulfoxide, sulfone, phosphoryl, trihalomethyl, and the like.

An aromatic radical is any benzenoid or non-benzenoid aromatic radical having a valence of 2 to 8. A non-benzenoid aromatic radical excludes simple phenyl groups, but includes aromatic, polynuclear aromatic, other carbocyclic aromatic radicals (e.g. those having cycloaliphatic groups), and heterocyclic aromatic radicals. For purposes of this invention, a substituted aromatic radical is any benzenoid or non-benzenoid aromatic radical having a valence of from 2 to 6 wherein one or more hydrogen atoms is replaced by an atom or a group of atoms other than hydrogen including the alkyl, alkenyl, alkoxy, halogens, nitrogen, sulfur, oxygen, and phosphorus or groups of heteroatoms such as nitro, sulfonic acid, $C_{1-10}$ alkyl sulfonate ester, sulfoxide, sulfone, phosphoryl, trihalomethyl, and the like. Such an aromatic radical also includes those radicals which contain other aliphatic moieties, aromatic groups, and/or hetero atoms.

In preferred embodiments, $R^4$ has at least seven carbons and, in more preferred embodiments, is ethylenically unsaturated. This ethylenic unsaturation should be copolymerizable with the acrylamido group defined by $R^1$, $R^2$, and $R^3$, e.g. an acrylamido group. The size of the group will affect the physical properties of a polymer prepared therefrom such that a larger $R^4$ group will impart different physical properties than a smaller group. For example, a higher alkyl group as (or part of) the $R^4$ group will tend to impart greater flexibility to the polymer.

The B linking group, if present, is introduced into the molecule by the derivatization of one of the piperazine nitrogen atoms. The B linking group is a carbonyl, sulfonyl, amide, or carboxyl group, i.e. a group having the respective formula:

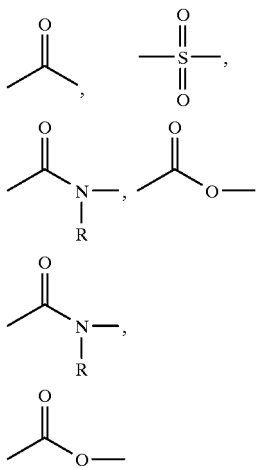

In each respective case, the compound will then have at that piperazine nitrogen atom an amide functionality, a sulfonamide functionality, a substituted-urea functionality, or a urethane functionality. Because the piperazine nitrogen atom can be covalently bonded to the $R^4$ group directly, a B linking group may not be present and, thus, n may be zero (in which case there will be a tertiary amine functionality at that piperazine nitrogen atom).

To prepare the compounds of this invention, piperazine is reacted with two different derivatizing agents, the identity of each being determined by the desired structures of $R^1$, $R^2$, and $R^3$, and $R^4$ (and the B linking group, if present), and the leaving group (if any) in these derivatization reactions. Thus, one of the derivatizing agents will have the following formula VI:

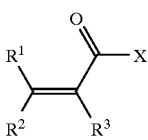

wherein $R^1$, $R^2$, and $R^3$ are as defined above and X is a leaving group (e.g. a halogen such as chlorine or another displacable anion-forming atom or group, e.g. a carboxylate group when the acylating agent is an acid anhydride). The other agent will have the formula VII:

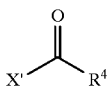

wherein $R^4$ is as defined above and X' is a leaving group (e.g. as set forth above). Of course, when the derivatizing agent is an isocyanate, i.e. that used to form a substituted-urea functionality, there is no "leaving group" as such in the strictest sense because the nitrogen atom of the isocyanate reactant, does not leave the molecule.

The reactions of the piperazine compound and the derivatizing agents may be conducted sequentially or simultaneously, depending on whether the two acylating agents are compatible. In a simultaneous reaction, both agents will be mixed with the piperazine compound under conditions which will cause the reaction to proceed as follows in scheme 1:

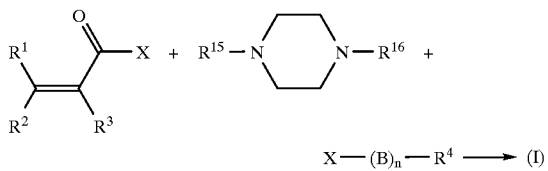

wherein $R^1$, $R^2$, $R^3$, $R^4$, X and X' are as defined above.

If one of the derivatizing agents has a higher reactivity for piperazine than the other derivatizing agent and this higher reactivity cannot be practicably compensated for (e.g. by adjusting the ratio of derivatizing agents in the reaction mixture), or if the derivatizing agents will react with each other to any degree that will provide an unacceptable by-product (e.g. if $R^8$ contains a hydroxyl or amine group susceptible to acylation), then the reactions will be performed sequentially. For example, if $R^4$ contains a hydroxyl or amine function, then a reaction sequence according to scheme 2 may be employed:

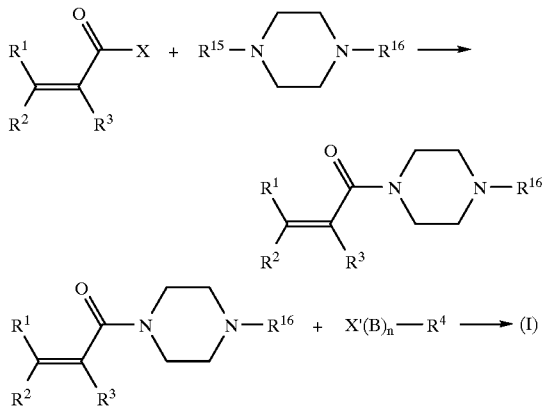

wherein $R^{15}$ and $R^{16}$ are hydrogen or an organic group susceptible of displacement in the acylating reaction and the other groups are as defined above.

The reaction to introduce the acrylamide functionality into the molecule is an acylation reaction. Acylation techniques for amide formation are generally described in *Encyclopedia of Chemical Technology*, vol. 2, pp. 252–258 (Kirk-Othmer, eds., John Wiley & Sons, Inc., N.Y., N.Y., 1978), and in R. Larock, *Comprehensive Organic Transformations: A Guide to Functional Group Preparations*, pp. 978 and 979 (VCH Publishers, N.Y., N.Y., 1989) the disclosures of which are incorporated by reference. In the acylation of an amine, an acylating compound of the desired molecular formula with a leaving group is reacted with the amine compound. For example, a carboxylic acid, acid anhydride or acid halide (e.g., chloride, of acrylic or methacrylic acid) is reacted with the amine, or derivative thereof, optionally in the presence of a catalyst, e.g. N,N-dimethylaminopyridine (typically in an amount of from about 0.001% to about 5%, more typically from about 0.01% to about 2% by weight of the combined weight of the reactants). When the carboxylic acid form of the acylating agent (i.e. leaving group is a hydroxyl group) is used, a strong acid catalyst, e.g. p-toluenesulfonic acid, is typically employed.

The reaction is typically accomplished in an inert solvent, but the catalyst or one of the reactants may also act as a solvent. Because piperazine is hydrophilic, but the reaction product tends to be less so, the choice of solvent and reaction conditions can affect the efficiency of the reaction. Generally, it has been found that an organic solvent having a greater polarity than an aromatic solvent (e.g. toluene) is preferred, for example, a mixture of acetonitrile and dichloromethane (e.g. 1:1 by volume) is a preferred solvent.

Because piperazine is a secondary amine, an acylating agent with a more labile leaving group (e.g. an acid halide wherein the leaving group is a halogen anion such as chloride) is preferred. With such a leaving group, a hydrohalic acid (e.g. hydrochloric acid) is a by-product of the reaction, and thus, an alkaline material should be added to the reaction mixture to neutralize by-product acid. It has been found that inorganic alkaline materials, e.g. alkali metal carbonates, are less preferred due to problems associated with product isolation and that lower alkyl tertiary amine bases (having the formula $NR^1R^2R^3$ wherein $R^1$, $R^2$, and $R^3$ are independently $C_1$ to $C_4$ alkyl, e.g. triethylamine) are useful in neutralizing acid formed during an acylation reaction which employs an acyl halide as the acylating agent.

It should also be noted that when an ester functional compound is prepared as a result of the use of an anhydride as an acylating agent (e.g. when phthalic anhydride is used as an acylating agent to introduce the $R^4$ group into the molecule), the leaving group will be a carboxyl anion that is covalently bonded to $R^8$. Thus, the carboxyl group must, in this case, be esterified to introduce the $R^{11}$ group into the molecule. Conventional esterification techniques which employ an alcohol having the formula $R^{11}$—OH, or an ester thereof that is susceptible to transesterification, will be useful to esterify the carboxyl anion that is created upon the opening of the anhydride linkage. Alternatively, the alcohol $R^{11}$—OH can be reacted with an anhydride to prepare an intermediate that has both ester and carboxyl functionality. The carboxyl functionality of this intermediate can then be used as an acylating agent in schemes 1 and 2. If the alcohol $R^{11}$—OH is a polyol, then the reaction of a molar amount of the anhydride equal to the polyol functionality can be used to prepare an intermediate that has sufficient carboxyl functionality to introduce a piperazine functionality into the molecule that is equal to the polyol functionality, followed by reaction of the n-functional piperazine intermediate with a derivatizing agent of formula VI to introduce one or more ethylenic unsaturations into the molecule, i.e. as set forth in the following scheme:

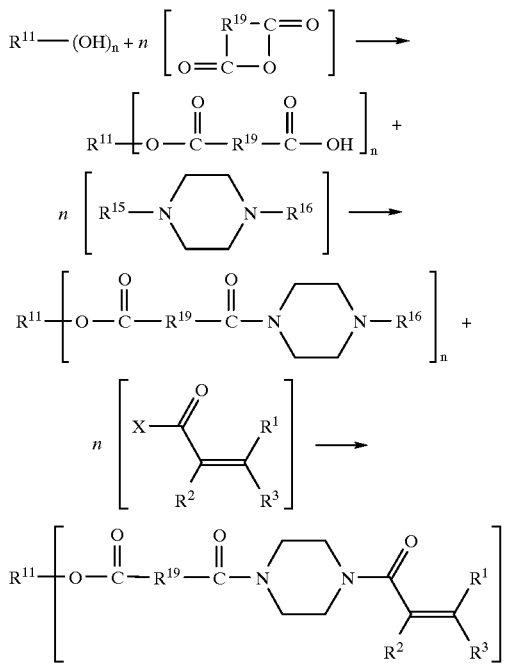

wherein $R^{19}$ is the residue of an organic dicarboxylic acid anhydride.

Examples of the anhydrides that can be used as an acylating agent (or half-esters thereof) include substituted succinic anhydrides which are preferred due to their low viscosity at room temperature. The low viscosity at room temperature leads to advantages in the final product (i.e. liquid final products) as well as in the synthetic procedure (i.e. a stirrable liquid that can serve as a reactant and thus provide a liquid reaction medium without the addition of a solvent). Preferred substituted succinic anhydrides are the alkyl- or alkenyl-substituted succinic anhydrides, e.g. n-octenyl succinic anhydride, n-nonenyl succinic anhydride, dodecenyl succinic anhydride, and iso-octadecenyl succinic anhydride.

The choice of the reactant $X-(B)_n-R^4$ will determine the nature of the B linking group that is introduced into the molecule. When there is no B linking group, the reactant will typically be an alkyl halide or an aryl alkaline earth metal halide (e.g. the Grignard reagent phenyl magnesium bromide). Alkylation of amines is discussed in *Encyclopedia of Chemical Technology*, vol. 2, pp. 67 and 68 (Kirk-Othmer, eds., John Wiley & Sons, Inc., N.Y., N.Y., 1978), the disclosure of which is incorporated by reference. When the B linking group is a carbonyl group, the reactant will typically be an acid halide and the product can be characterized as a acylamide. Acylation reactions are discussed in *Encyclopedia of Chemical Technoloay*, vol. 2, pp. 252–258 (Kirk-Othmer, eds., John Wiley & Sons, Inc., N.Y., N.Y., 1978), the disclosure of which is incorporated by reference. When the B linking group is a sulfonyl group, the reactant will typically be a sulfonyl halide and the product can be characterized as a sulfonamide. The reaction to form a sulfonamide is very similar to an acylation reaction. The synthesis of sulfonamides is discussed in *Encyclopedia of Chemical Technology*, vol. 2, pp. 795 and 803–806 (Kirk-Othmer, eds., John Wiley & Sons, Inc., N.Y., N.Y., 1978), the disclosure of which is incorporated by reference.

As discussed above, when the B linking group is an amide, the reactant will typically be an isocyanate. The synthesis of urea compounds by the reaction of an amine with an isocyanate is discussed in *Encyclopedia of Chemical Technology*, vol. 12, pp. 319–321 (Kirk-Othmer, eds., John Wiley & Sons, Inc., N.Y., N.Y., 1980), the disclosure of which is incorporated by reference.

Further, when the B linking group is a carboxylate group such that the compound has a urethane functionality, a reaction sequence as shown in scheme 3, below will be useful:

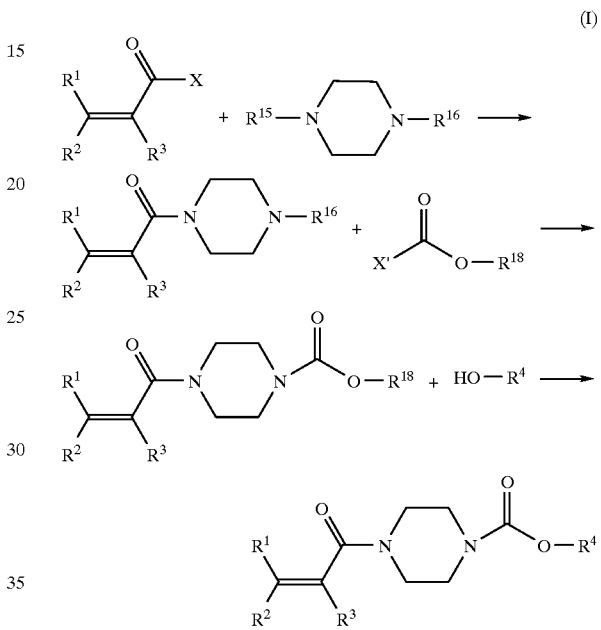

wherein all of the variables are as set forth above and $R^{18}$ is a group susceptible to transesterification, e.g. an alkoxy group or an aryloxy group, preferably lower alkoxy (e.g. a methoxy group). Transesterification reactions are generally known. They are typically catalyzed by a base (e.g. alkali) or an acid and are governed by principles of mass transfer so that the reaction can be driven to substantial completion by removal of the by-product alcohol $R^{18}$—OH (e.g. by distillation). Transesterification reactions are discussed in *Encyclopedia of Chemical Technology*, vol. 9, pp. 306–308 (Kirk-Othmer, eds., John Wiley & Sons, Inc., N.Y., N.Y., 1980), the disclosure of which is incorporated by reference.

In the special case where $R^4$ has the formula IV, i.e. there are two piperazine groups in the molecule, it is convenient to employ the following scheme 4 to prepare the compound:

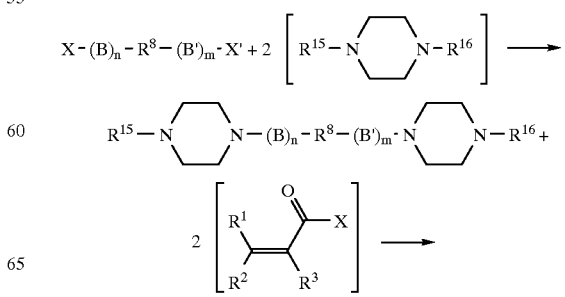

-continued

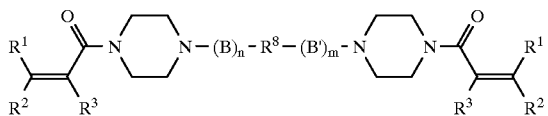

wherein the groups are selected as set forth above. It should be noted that the $R^1$, $R^2$, and $R^3$ groups on each end of the molecule need not be the same, i.e. if, for example, a mixture of acryloyl chloride and methacryloyl chloride are used to acylate the di-piperazine intermediate in scheme 4 above, the $R^1$, $R^2$, and $R^3$ groups on one end of the molecule will differ from the $R^1$, $R^2$, and $R^3$ groups on the other end of the molecule. The $R^8$ group is derived from a di-carboxylic acid compound, preferably a di-carboxylic acid having a higher alkylene group between the acid groups, or a reactive derivataive thereof, e.g. an anhydride, an acid halide, or transesterifiable ester thereof. Examples of diacids include aliphatic diacids, e.g. succinic acid and substituted succinic acids (as described below, and aromatic diacids, e.g. phthalic acid. Preferred diacids having a higher alkylene chain are described in *Encyclopedia of Polymer Science and Technology*, vol. 11, pp. 476–489, (John Wiley & Sons, Inc. N.Y., N.Y., 1988), the disclosure of which is incorporated herein by reference. Such preferred diacids include dimer acids (produced by the dimerization of fatty acids that results in an $R^8$ group which is a divalent hydrocarbon, e.g. oleic acid that results in an $R^8$ group which is a divalent hydrocarbon having 36 carbon atoms), tridecanedioc acid (produced by the ozonolysis of erucic acid), $C_{19}$ diacid (produced by the hydroformylation of oleic acid with carbon monoxide) and $C_{21}$ diacid (produced by the reaction of tall oil fatty acid with acrylic acid). The preferred diacids are dimer acids. Dimer acids are also described in detail in U.S. Pat. No. 5,138,027 (Van Beek), the disclosure of which is incorporated herein by reference. The compounds of formula II can be considered compounds of formula I wherein $R^4$ is a substituted aliphatic group, e.g. when $R^8$ is derived from a dimer acid such that $R^4$ is a higher alkyl group substituted with an acrylamido-piperazinyl-carbonyl group.

In the special case of compounds of formula III, i.e. there are two piperazine groups in the molecule and an $R^{17}$ group, it is convenient to employ the following scheme 5 to prepare the N,N'-diacylamido-piperazine compound:

wherein the groups are selected as set forth above. It should be noted that the $R^1$, $R^2$, and $R^3$ groups on each end of the molecule need not be the same; if, for example a mixture of acryloyl chloride and methacryloyl chloride are used to acylate the di-piperazine intermediate in scheme 5 above, the $R^1$, $R^2$, and $R^3$ groups on one end of the molecule will differ from the $R^1$, $R^2$, and $R^3$ groups on the other end of the molecule. The reactant HO—$R^{17}$—OH is a polyol reactant. Examples of polyols are polyalkyleneoxy compounds, e.g. those described in *Encyclopedia of Polymer Science and Technology*, vol. 6, pp. 225–322 (John Wiley & Sons, Inc., N.Y., N.Y. 1986), the disclosure of which is incorporated herein by reference. Preferred polyols are alkyleneoxyalkyl or alkyleneoxyaralkyl compounds having at least two free hydroxyl groups. Examples of alkyleneoxyalkyl compounds are ethoxylated and/or propoxylated lower alkane polyols, e.g. propoxylated trimethylolpropane (e.g. Photonol PHO-7072), ethoxylated trimethylolpropane (e.g. Photonol PHO-7149, Photonol PHO-7155, and Photonol PHO-7158), propoxylated glycerol (e.g. Photonol PHO-7094), propoxylated neopentylglycol (e.g. Photonol PHO-7127), and ethoxylated neopentylglycol (e.g. Photonol PHO-7160). Examples of alkyleneoxyaralkyl compounds are ethoxylated and/or propoxylated alkylpolyphenols, e.g. propoxylated bisphenol A (e.g. Photonol PHO-7020) and ethoxylated bisphenol A (e.g. Photonol PHO-7025, and Photonol PHO-7028). All of these Photonol products are available commercially from Henkel Corporation, Ambler, Pa.

The polymerizable components useful in this invention are any materials which are capable of addition copolymerization with the N,N'-diacylamido-piperazine compounds of formula I described above to form a useful polymer composition. The polymerization of acrylamide monomers is discussed in *Encyclopedia of Polymer Science and Engineering*, vol. 1, pp. 169–211 (John Wiley & Sons, Inc., N.Y., N.Y., 1985), the disclosure of which is incorporated by reference. The polymerizable components include mono-ethylenically unsaturated monomers capable of homopolymerization, or copolymerization with other ethylenically unsaturated monomers, as well as copolymerization with the compound. Examples of suitable mono-ethylenically unsaturated compounds include alkyl acrylates, alkyl methacrylates, vinyl esters, vinyl amines and vinyl aromatic compounds. Specific examples include ethyl acrylate, t-butyl acrylate, 2-ethylhexyl acrylate, methyl methacrylate, lauryl methacrylate, vinyl acetate, N-vinyl pyrrolidinone, styrene, and vinyl toluene.

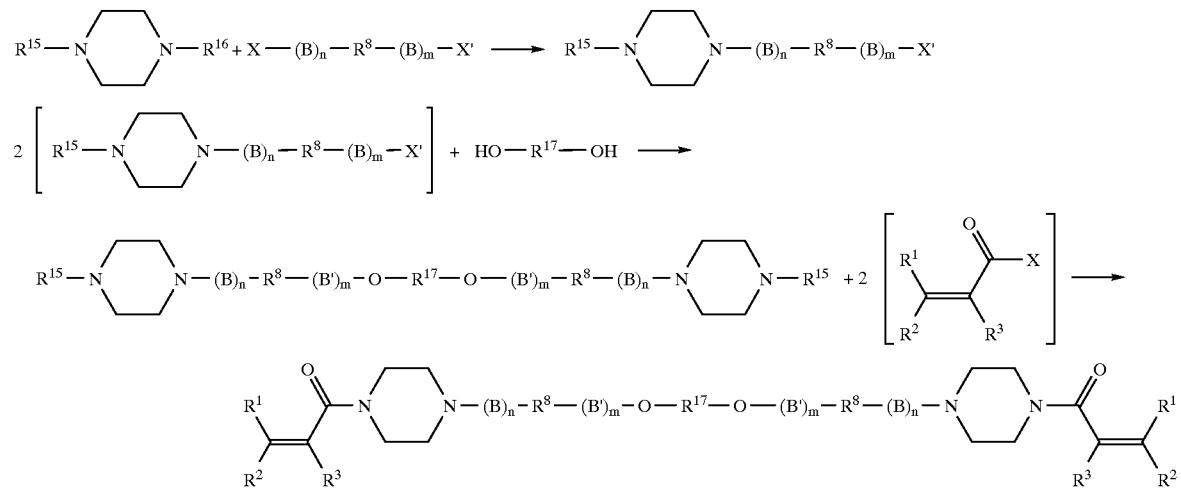

Polymerizable compounds which may be used in the present invention are addition-polymerizable monomers and oligomers and polymers thereof. Addition-polymerizable monomers are compounds having one or more carbon-carbon unsaturated bonds. Examples of the compounds are acrylic acid and salts thereof, acrylates (e.g. lower alkyl acrylates), acrylamides (e.g. lower N-alkyl acrylamides), methacrylic acid and salts thereof, methacrylates, methacrylamides, maleic anhydride, maleates, itaconates, styrenes, vinyl ethers, vinyl esters, N-vinyl-heterocyclic compounds, allyl ethers, and allyl esters and derivatives thereof.

In addition, a crosslinking compound having an activity of increasing the degree of hardening or the viscosity of the formed polymeric compounds, by crosslinking the polymeric coating, can be employed. Such crosslinking compounds are so-called poly-functional monomers having a plurality of ethylenic or vinyl groups or vinylidene groups in the molecule. This addition will be especially useful if the N,N'-substituted acylamido-piperazine compound chosen has only one ethylenic unsaturation, e.g. N-(o-alkyl-phthalamido), N'-acrylamido-piperazine.

Examples of a number of the various polymerizable compounds which may be included in the polymerizable compositions of the present invention include acrylic acid, methacrylic acid, butyl acrylate, methoxyethyl acrylate, butyl methacrylate, acrylamide, N, N-dimethylacrylamide, N, N-diethylacrylamide, N-acrylamido-morpholine, N-acrylamido-piperidine, glycidyl acrylate, 2-ethylhexyl acrylate, acrylic acid anilide, methacrylic acid anilide, styrene, vinyltoluene, chlorostyrene, methoxystyrene, chloromethylstyrene, 1-vinyl-2-methylimidazole, 1-vinyl-2-undecylimidazole, 1-vinyl-2-undecylimidazoline, N-vinylpyrrolidone, N-vinylcarbazole, vinylbenzyl ether, vinylphenyl ether, methylene-bis-acrylamide, trimethylene-bis-acrylamide, hexamethylene-bis-acrylamide, N, N'-diacrylamidopiperazine, m-phenylene-bis-acrylamide, p-phenylene-bis-acrylamide, ethylene glycol diacrylate, propylene glycol dimethacrylate, diethylene glycol diacrylate, polyethylene glycol diacrylate, bis(4-acryloxypolyethoxyphenyl)propane, 1,5-pentanediol diacrylate, neopentyl glycol diacrylate, 1,6-hexanediol acrylate, polypropylene glycol diacrylate, pentaerythritol triacrylate, trimethylolpropane triacrylate, pentaerythritol tetraacrylate, N-methylol-acrylamide, diacetone-acrylamide, triethylene glycol dimethacrylate, pentaerythritol tetra-allyl ether.

Examples of useful reactive oligomers include low molecular weight polymers (e.g., about 1,000 to 25,000 g/mole) having polymerizable ethylenic unsaturation. Specific examples include maleic-fumaric unsaturated polyesters, acrylate-terminated polyesters (e.g. those described in U.S. Pat. No. Re 29,131 to Smith et al.) acrylic copolymers having pendant vinyl unsaturation (e.g. allyl acrylate/acrylic copolymers), epoxy acrylates, and polyurethane acrylates.

Examples of useful reactive polymers include graft polymerizable polyolefins, e.g., polyethylene, polypropylene, and ethylene/propylene copolymers, and polymers having polymerizable ethylenic unsaturation along the backbone, for example diene homopolymers or copolymers (e.g., styrene-butadiene copolymers, cis-polybutadiene, and butadiene-acrylonitrile copolymers).

The polymerizable component and N,N'-acylamido-piperazine compound can be mixed in any convenient manner which will place the component and compound in a sufficiently reactive association to form a polymer on subsequent curing thereof. Generally, simple mixing of the polymerizable component and N,N'-acylamido-piperazine compound will suffice. Other useful techniques include conventional wet chemistry techniques, e.g., dissolution in a common solvent system.

The amount of the N,N'-acylamido-piperazine compound in the polymerizable composition will vary depending upon the contemplated application of the cured polymeric composition, but will generally be sufficient to detectably affect the properties of the polymer and/or crosslink the polymeric composition. The affect on the properties of the polymer and/or degree of crosslinking of the cured polymeric composition can be determined by conventional techniques, e.g., adhesion to substrates, resistance to solvents (e.g., swelling, extractibles, and/or spot-testing). In preferred compositions, the amount of a diacrylamido-piperazine compound will be sufficient to measurably increase the gel content of the cured polymeric composition, e.g., preferably by at least about 1% and more preferably at least about 5%. Typical levels of N,N'-acylamido-piperazine compound that have only one ethylenic unsaturation will range from about 5 mole % to about 90 mole %, preferably from about 10 mole % to about 50 mole %, of the polymerizable components of the polymerizable composition.

The polymerizable composition of the present invention can be applied to a variety of substrates. These include, for example, porous stock such as paper and cardboard, wood and wood products, metals such as aluminum, copper, steel, and plastics such as P.V.C., polycarbonates, acrylic and the like. After addition of a suitable photoinitiator, e.g., PHOTOMER 51® brand photoinitiator (benzyl dimethyl ketal), the compositions are applied by methods such as spraying, rollcoating, flexo and gravure processes onto a selected substrate. The resulting coated substrate, e.g., a paper, is typically cured under a UV or electron beam radiation. The compositions may optionally include other substances such as pigments, resins, monomers and additives such as antioxidants and rheological modifiers. For example, flow and levelling agents, e.g. BYK-307 and/or BYK 310, available form BYK-Chemie USA, Wallingford, Conn., can be used to modify the coating characteristics of the polymerizable composition. Methods of coating and materials used in coatings are described in *Encyclopedia of Polymer Science and Engineering*, vol. 3, pp. 552–671 and supp. vol., pp. 53, 109 and 110 (John Wiley & Sons, Inc., N.Y., N.Y., 1985), the disclosure of which is incorporated by reference.

The coated surface is then exposed to sufficient energy, e.g. heat or electromagnetic radiation to cure the composition through the reactive pi bonds. Suitable sources of radiation include ultraviolet light, electron beam or radioactive sources such as are described in U.S. Pat. No. 3,935,330 issued Jan. 27, 1976 to Smith et al. To enhance the rate of curing free radical initiators may be included in the composition such as benzoin, benzoin ethers, Michier's Ketone and chlorinated polyaromatic hydrocarbons. Other free radical initiators are ordinarily organic peroxides, hydroperoxides, peroxy acids, peroxy esters, azo compounds, ditertiary butyl peroxide, benzoyl peroxide, 2,4-dichlorobenzoyl peroxide, tertiary butyl hydroperoxide, 1,5-dimethyl-2,5-bis (hydroperoxy)-hexane, peroxyacetic acid, peroxybenzoic acid, tertiary butyl peroxypivalate, tertiary butyl peroxyacetic acid and azobisisobutyronitrile. The free radical initiator is typically present at from about 0.01 to about 20% by weight of the radiation curable components. To ensure that the composition does not prematurely polymerize, a free radical inhibitor may be added to the polymerizable composition. Examples of suitable inhibitors include hydroquinone and the methyl ether thereof or butylated hydroxy toluene at a level of from about 5 ppm to about 2000 ppm by weight of the polymerizable components.

Particularly preferred sources of radiation emit electromagnetic radiation predominantly in the ultra-violet band. When such a source is used, the polymerizable composition preferably contains a photoinitiator susceptible to ultra-violet radiation, e.g. benzoin, benzoin ethers, alpha, alpha-dimethoxy-alpha-phenylacetophenone, diethoxyacetophenone, alpha-hydroxy-alpha,alpha-dimethylacetophenone, and 1-benzoylcyclohexanol.

The amount of radiation necessary to cure the composition will of course depend on the angle of exposure to the radiation, the thickness of the coating to be applied, and the amount of polymerizable groups in the coating composition, as well as the presence or absence of a free radical initiating catalyst. For any given composition, experimentation to determine the amount of radiation sensitive pi bonds not cured following exposure to the radiation source is the best method of determining the amount and duration of the radiation required. Typically, an ultra-violet source with a wavelength between 200 and 300 nm (e.g. a filtered mercury arc lamp) is directed at coated surfaces carried on a conveyor system which provides a rate of passage past the ultra-violet source appropriate for the radiation absorption profile of the composition (which profile is influenced by the degree of cure desired, the thickness of the coating to be cured, and the rate of polymerization of the composition).

The polymerizable compositions of this invention may also find use as a starting material for applications in addition to coatings. Particular examples include articles formed by the shaping (e.g. casting, molding, or extrusion) of polymeric materials, as well as binders (e.g. for pigments of printing inks, magnetic media, etc.), or by use of the composition as an adhesive or sealant. Further, steric polymerization techniques as described by E.J. Murphy et al., "Some Characteristics of Steric Polymerization", *Proceedings of RadTech 1990—North America*, vol. I, pp. 217–226, the disclosure of which is incorporated herein by reference, may be useful. In such techniques, where a pool of polymerizable composition is subjected to a focused laser beam of ultra-violet radiation, an object is formed within the pool from discrete thin layers formed at the top of the pool where the laser beam is focused. In a sense, the composition polymerizes in contact with the surface of a layer of cured polymer. The particular procedures used and the choice of the other necessary or desirable starting materials, catalysts, and other functional additives, as well as the amount of N,N'-acylamido-piperazine compound, will be within the skill of the art within which the crosslinked polymeric composition is employed.

U.S. Ser. No. 08/242,797, filed May 19, 1994, U.S. Pat. No. 5.565.567 which is a continuation-in-part of U.S. Ser. No. 08/073,014, filed Jun. 4, 1993, now abandoned, the disclosures of which are incorporated herein by reference, discloses acrylamido-piperazine compounds useful in radiation curable coatings.

The following examples will serve to further illustrate the invention, but should not be construed to limit the invention, unless expressly set forth in the appended claims. All parts, percentages, and ratios are by weight unless otherwise indicated in context.

EXAMPLES

Coating Procedures and Apparatus

In the following examples, coatings were prepared by the following procedure. The substrates used, unless noted otherwise, were aluminum panels available commercially as Q-panels from Q-Panel Corporation, and are coated using RDS Coating Rods. The curing apparatus was a Fusions Systems Model F440 with a 300 watt/inch mercury bulb. The variables in the tests include the speed of the belt which transports the substrate under the bulb, the number of passes the substrate makes under the bulb, and the thickness of the coating on the substrate, and variations in the coating formulation, e.g. type and amount of additives and co-monomers, which will be noted below.

Example 1

The compound N-acrylamido-N'-(n-butyl phthalamido)-piperazine was prepared using the specific procedure set forth therebelow. The compound was then used to form a coating by the procedure set forth below.

Procedure for the Synthesis of Phthalic Piperazine Amide Acid

Into a 3 liter, four-necked round-bottom flask fitted with mechanical stirring, dry nitrogen and a reflux condenser were charged 129.2 grams piperazine, 750 ml dichloromethane, 750 ml acetonitrile, and 6.1 grams dimethylaminopyridine. To this mixture was added portion-wise 222.2 g phthalic anhydride. Following the addition, the mixture was refluxed for 3 hours, at the end of which period no residual anhydride was present by infrared analysis. The solvent was decanted from the solid product precipitate.

Procedure for the Synthesis of Phthalic Piperazine Amide Acid Butyl Ester

To the precipitated product from the previous procedure were added 150 ml 12N HCl, 200 ml n-butanol, and 7.1 g p-toluenesulfonic Acid. A Dean-Stark trap was attached to the reflux condenser, and the reaction mixture was heated to reflux. The mixture was refluxed for 15 hours, at which time infrared analysis showed extensive conversion to the butyl ester, and TLC showed a single product using 1:1 methanol-water as eluent. The ester product was separated from the residual n-butanol by pressure filtration.

Procedure for the Synthesis of Phthalic Piperazine Acrylamide Butyl Ester

Into a 3 liter, four-necked round-bottom flask fitted with a reflux condenser dry air, and mechanical stirring, were charged 324 g of the ester from the previous procedure, 500 ml acetonitrile, 250 ml dichloromethane, 253 g triethylamine, 3.0 g dimethylaminopyridine, and 0.21 g hydroquinone monomethyl ether. The mixture was cooled in an ice bath, and 100 g acryloyl chloride was added dropwise over a period of two and one half hours, with the addition rate sufficient to maintain a reaction temperature of 0–10 degrees C. The mixture was then allowed to warm to ambient temperature and stirred for an additional 90 minutes. The reaction mixture was then filtered through a Buchner funnel to remove undissolved solids. The resultant solution was washed with 1N HCl to remove unreacted triethylamine, dried with anhydrous sodium sulfate, and stripped of solvent under reduced pressure.

Procedure for Coating with Phthalic Piperazine Acrylamide Butyl Ester

A coating formulation was prepared by mixing 93 parts by weight of the neat phthalic piperazine acrylamide butyl ester, and 7 parts by weight of a photoinitiator blend consisting of 4 parts by weight of Darocure 1173, a photoinitiator available from Ciba-Geigy, Hawthorne, N.Y., 2 parts by weight of Photomer 81, a liquid form of benzophenone available from Henkel Corporation, Ambler, Pa., and 1 part by weight of triethanolamine. This composition was coated at 6.86 micrometers thickness and cured in one pass at 100 ft./min. The resulting coating exhibited a pencil hardness of 2H and dissolved with two methyl ethyl ketone (MEK) rubs. The resistance to MEK could be improved by the inclusion of a di-ethylenically unsaturated monomer, e.g. N,N'-bis-acrylamido piperazine.

Example 2

The compound bis-(N'-acrylamido-piperazinyl) dimer acid amide was prepared using the specific procedures set forth therebelow. The compound was then used to form a coating by the procedure set forth below.

Procedure for the Synthesis of EMPOL 1008 Acid Chloride

Into a 1 liter, four-necked round-bottom flask fitted with a magnetic stirrer, reflux condenser, thermometer, and dry nitrogen were charged 250.0 grams of EMPOL 1008, 250 ml hexane, and 2 ml dimethylformamide. To the stirred mixture was added 115.7 g thionyl chloride dropwise through an addition funnel over a period of 30 minutes. No exotherm was noted, however significant bubbling was noted. Infrared spectroscopic analysis of the reaction mixture showed approximately 50% conversion to the acid chloride after 1 hour, with complete conversion after stirring the mixture overnight.

Procedure for the Synthesis of EMPOL 1008 Piperazine Amide

Into a 2 liter, four-necked round-bottom flask fitted with a Dean-Stark trap, reflux condenser, and mechanical stirrer were charged 1000 ml toluene, 152.3 grams piperazine, and 134.4 grams potassium carbonate. The mixture was refluxed for 30 minutes to dry the reactants. The reaction mixture was then cooled to 10 degrees C. in an ice bath, and 250 ml dichloromethane was added to aid stirring. The Empol 1008 acid chloride was added dropwise through an addition funnel at a rate sufficient to maintain a reactant temperature of 10–15 degrees C. Following the addition, the mixture was allowed to warm to ambient temperature and stirred overnight. This material was then immediately converted to the acrylamide.

Procedure for the Synthesis of EMPOL 1008 Piperazine Acrylamide

To the stirred reaction flask of the previous procedure was added 201.5 grams potassium carbonate. The reaction mixture was cooled in an ice bath to 12 degrees C., and 132.0 grams acryloyl chloride was added dropwise over a period of 1 hour, maintaining a reactant temperature of 8–10 degrees C. The reaction mixture was pressure filtered through Celite to remove insoluble salts.

Procedure for Coating with EMPOL 1008 Piperazine Acrylamide

A coating formulation was prepared by mixing 93 parts by weight of the neat Empol 1008 piperazine acrylamide, and 7 parts by weight of a photoinitiator blend consisting of 4 parts by weight of Darocure 1173, a photoinitiator available from Ciba-Geigy, Hawthorne, N.Y., 2 parts by weight of Photomer 81, a liquid form of benzophenone available from Henkel Corporation, Ambler, Pa., and 1 part by weight of triethanolamine. This composition was coated at 6.86 micrometers thickness and cured in one pass at 100 ft./min. The resulting coating exhibited a pencil hardness of 2H dissolved with four methyl ethyl ketone (MEK) rubs, zero adhesion by a rudimentary test (in simple peel test with adhesive tape all of the coating in contact with the tape lifted from the substrate) and exhibited a Mandrel of less than 0.27. The resistance to MEK could be improved by the inclusion of a di-ethylenically unsaturated monomer, e.g. N,N'-bis-acrylamido piperazine. A second coating at 76.2 micrometers thickness was cured in one pass at 100 ft./min. The resulting coating exhibited a pencil hardness of 2H dissolved with forty-five methyl ethyl ketone (MEK) rubs, and zero adhesion.

Example 3

A compound was prepared by the same (or substantially similar) procedure of Example 2, with the exception that dodecanedioic acid was employed to prepare a compound in accordance with scheme 3 wherein $R^8$ is the divalent alkylene radical having the formula —$(CH_2)_{10}$—. A coating formulation was prepared by mixing 93 parts by weight of the dodecanedioic acid piperazine acrylamide, and 7 parts by weight of a photoinitiator blend consisting of 4 parts by weight of Darocure 1173, a photoinitiator available from Ciba-Geigy, Hawthorne, N.Y., 2 parts by weight of Photomer 81, a liquid form of benzophenone available from Henkel Corporation, Ambler, Pa, and 1 part by weight of triethanolamine. This composition was coated at 6.86 micrometers thickness and cured in one pass at 100 ft./min. The resulting coating exhibited a pencil hardness of 2H, dissolved after thirty-four methyl ethyl ketone (MEK) rubs, zero adhesion by a rudimentary test (in simple peel test with adhesive tape all of the coating in contact with the tape lifted from the substrate). A second coating at 76.2 micrometers thickness was cured in one pass at 100 ft./min. The resulting coating exhibited a pencil hardness of 2H dissolved only after greater than 100 methyl ethyl ketone (MEK) rubs, and zero adhesion. A third coating was prepared at 6.86 micrometers thickness, but at 800 ft./min. The cured coating had a pencil hardness of 5H and dissolved after six MEK rubs.

Example 4

A compound was prepared by the same (or substantially similar) procedure of Example 2, with the exception that adipic acid was employed to prepare a compound in accordance with scheme 3 wherein $R^8$ is the divalent alkylene radical having the formula —$(CH_2)_4$—. A coating formulation was prepared by mixing 93 parts by weight of the adipic acid piperazine acrylamide, and 7 parts by weight of a photoinitiator blend consisting of 4 parts by weight of Darocure 1173, a photoinitiator available from Ciba-Geigy, Hawthorne, N.Y., 2 parts by weight of Photomer 81, a liquid form of benzophenone available from Henkel Corporation, Ambler, Pa, and 1 part by weight of triethanolamine. This composition was coated at 6.86 micrometers thickness and cured in one pass at 100 ft./min. The resulting coating exhibited a pencil hardness of 2H and zero adhesion by a rudimentary test (in simple peel test with adhesive tape, all of the coating in contact with the tape lifted from the substrate) and exhibited a Mandrel of less than 0.27. A second coating at 76.2 micrometers thickness was cured in one pass at 100 ft./min and exhibited a pencil hardness of 2H with 50% adhesion. A third coating was prepared at 6.86 micrometers thickness, but at 800 ft./min. The cured coating had a pencil hardness of 2H.

Example 5

Coatings were prepared using N,N'-bis-acrylamido-piperazine as the only polymerizable monomer. A coating formulation was prepared by mixing 93 parts by weight of the piperazine bis-acrylamide, and 7 parts by weight of a photoinitiator blend consisting of 4 parts by weight of Darocure 1173, a photoinitiator available from Ciba-Geigy, Hawthorne, N.Y., 2 parts by weight of Photomer 81, a liquid form of benzophenone available from Henkel Corporation, Ambler, Pa, and 1 part by weight of triethanolamine. This composition was coated at 6.86 micrometers thickness and cured in one pass at 100 ft./min. The resulting coating exhibited a pencil hardness of 2H and zero adhesion by a rudimentary test (in simple peel test with adhesive tape, all of the coating in contact with the tape lifted from the substrate) and exhibited a Mandrel of zero. A second coating at 76.2 micrometers thickness was cured in one pass at 100 ft./min and exhibited a pencil hardness of 2H with zero adhesion.

Example 6

Alternate Procedure for the Synthesis of EMPOL 1008 Piperazine Amide

Into a flask fitted with a distillation head and mechanical stirrer were charged 459.8 grams of Empol 1008 dimer acid, 12 ml of water and 4 drops of an inert anti-foam (from Dow Chemical). To this mixture was added 140.2 grams piperazine (a molar ratio of piperazine to dimer acid of about 2:1). The resulting mixture was heated to 126° C. over about 25 minutes and then to about 160° C. over about 65 minutes and held at about 160° C. for about 15 minutes. Then 4 drops of 85% phosphoric acid was added and the mixture was held at about 160° C. for one hour. After one hour, 36 ml of water had distilled over. Infra-red analysis of the mixture showed a residual carboxylate peak. The mixture was heated to 175° C. and held over about 70 minutes after which the infra-red analysis still showed a very small carboxylate peak. The mixture was heated to 200° C. and held over about 130 minutes after which the infra-red analysis showed no remaining carboxylate.

Example 7

Synthesis of a Diester of Polybutyleneoxy glycol with N'-Acryloyl-N-(n-octenylsuccinoyl)-piperazine A compound having the following formula was prepared:

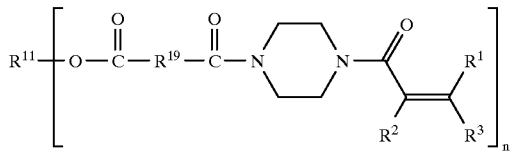

wherein $R^{11}$ is the residue of an alpha,omega-butyleneoxy glycol, $R^{19}$ is the residue of n-octenylsuccinic anhydride, n is 2 and $R^1$, $R^2$, and $R^3$ are all hydrogen.

Into a 1 liter resin kettle fitted with mechanical stirrer and dry nitrogen gas were charged 250.0 grams of a polybutyleneoxy glycol (available from Dow Chemical, Midland, Mich., as B100-1000 and having a molecular weight of about 1000 g/mole) 105.2 grams of n-octenylsuccinic anhydride, and 3.5 grams dimethylaminopyridine. The reaction mixture was heated to 100° C. until the anhydride was completely reacted as determined by infra-red analysis. The resulting diacid compound was then reacted with piperazine as set forth in the alternate procedure for the synthesis of EMPOL 1008 piperazine amide and the product was then converted to a diacrylamide compound by reaction with acryloyl chloride.

Example 8

The compound bis-(N'-acrylamido-piperazinyl) dimer acid amide was prepared by the following reactions. The compound was then used to form a coating by the procedure set forth below.

Procedure for the Synthesis of EMPOL 1008 Piperazine Amide

Into a flask with a nitrogen atmosphere fitted with a distillation head and mechanical stirrer were charged 69.5 parts by weight of Empol 1008 dimer acid, 21.1 parts by weight of piperazine (a molar ratio of piperazine to dimer acid of about 2:1), 2 parts by weight of water and 0.13 parts by weight of an inert anti-foam (from Dow Chemical). To this mixture was added 0.15 parts by weight of 85% phosphoric acid. The resulting mixture was heated to 160° C. and held at about 160° C. for about 2 hours. Then 0.15 parts of additional 85% phosphoric acid was added and the mixture was heated to 180° C. and held at about 180° C. for two hours. The mixture was then heated to 200° C. and held at about 200° C. for about 2 hours. The reaction is complete when the amine value of the mixture is between 125–130 and the acid value is between 0–10.

Procedure for the Synthesis of EMPOL 1008 Piperazine Acrylamide

To the cooled product of the preceding reaction was added 151 parts by weight of a mixture of ethyl acetate and cyclohexane (in a weight ratio of 1: 1), 0.4 parts by weight of the methyl ether of hydroquinone, and 25 parts by weight of triethylamine all under a dry nitrogen atmosphere. This mixture was cooled to 5° C. and 22.3 parts by weight of acryloyl chloride (the distillate of a reaction product of 29.5 parts by weight of acrylic acid and 48.8 parts by weight of thionyl chloride in equal parts by weight of additional ethyl acetate/cyclohexane solvent to make a 1:1 solution of acryloyl chloride in solvent) was added at a rate that maintains the reaction temperature of 5–15° C. After addition is complete, the reaction mixture was allowed to warm to room temperature. The reaction is allowed to continue until the product shows no absorption at 1800 cm$^{-1}$ by infra-red spectroscopy. The reaction mixture was then mixed with 62 parts by weight of water to dissolve suspended solids and the resulting lower aqueous layer was separated by gravity. The organic layer was then heated to 55–60° C. at reduced pressure to distill solvent to less than 0.2% by weight of the product.

Procedure for Coating with EMPOL 1008 Piperazine Acrylamide

A coating formulation was prepared by mixing 93 parts by weight of the neat Empol 1008 piperazine acrylamide, and 7 parts by weight of a photoinitiator blend consisting of 4 parts by weight of Darocure 1173, a photoinitiator available from Ciba-Geigy, Hawthorne, N.Y., 2 parts by weight of Photomer 81, a liquid form of benzophenone available from Henkel Corporation, Ambler, Pa, and 1 part by weight of triethanolamine. This composition was coated at 6.86 micrometers thickness and cured in one pass at 100 ft./min.

Example 9

The procedure of Example 8 can be repeated with the addition of 0.02 parts by weight of N,N-dimethylaminopyridine to the 151 parts by weight of a mixture of ethyl acetate and cyclohexane.

Example 10

The procedure of Example 8 can be repeated with the addition of 0.2 parts by weight of N,N-dimethylaminopyridine to the 151 parts by weight of a mixture of ethyl acetate and cyclohexane.

Example 11

The procedure of Example 8 can be repeated with the addition of 2.0 parts by weight of N,N- dimethylaminopyridine to the 151 parts by weight of a mixture of ethyl acetate and cyclohexane.

What is claimed is:

1. A composition having improved stability against gelation comprising a compound of the formula:

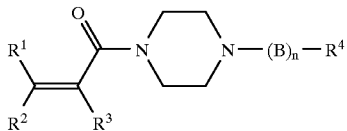
(I)

wherein:
$R^1$, $R^2$, and $R^3$ are each independently selected from the group consisting of hydrogen and lower alkyl,
B is a linking group selected from the group consisting of carbonyl, sulfonyl, amide, and carboxyl;
n is one or zero;
$R^4$ is a radical selected from the group consisting of a higher aliphatic group, a substituted higher aliphatic group, an alicyclic group, a heterocyclic group, a non-benzenoid aromatic group, and a substituted aromatic group, wherein viscosity of said composition does not increase more than 20% when the composition is held at 60° C. for 150 hours.

2. A composition of claim 1 wherein said $R^4$ is selected from the group consisting of alkyl groups having from about 5 to about 50 carbon atoms, substituted alkyl groups having from about 5 to about 50 carbon atoms, cycloalkyl groups having from about 5 to about 50 carbon atoms, and substituted phenyl groups having from 7 to about 50 carbon atoms.

3. A composition of claim 1 wherein n is one and B is a carbonyl group.

4. A composition of claim 1 wherein n is one and B is a sulfonyl group.

5. A composition of claim 1 wherein n is one and B is an amide group.

6. A composition of claim 1 wherein n is one and B is a carboxyl group.

7. A composition of claim 1 wherein n is zero.

8. A composition of claim 7 wherein $R^4$ has from 7 to about 50 carbon atoms.

9. A composition of claim 1 wherein $R^4$ has the formula —$R^8$—(B')$_m$—R, wherein $R^8$ is a divalent group selected from the group consisting of a higher alkylene group, a substituted higher alkylene group, an aromatic group, and a substituted aromatic group, B' is a linking group selected from the group consisting of carbonyl, sulfonyl, amide, and carboxyl, m is zero or one, and R is selected from the group consisting of an aliphatic group, a substituted aliphatic group, an alicyclic group, a heterocyclic group, an aromatic group, and a substituted aromatic group.

10. A composition of claim 1 wherein $R^4$ has at least seven carbons and is ethylenically unsaturated.

11. A composition of claim 1 wherein $R^4$ is selected such that the compound has the formula:

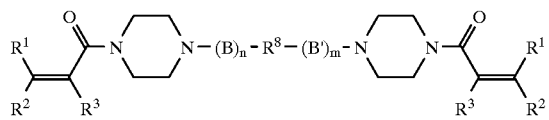

wherein
each $R^1$, $R^2$, and $R^3$ is independently selected from the group consisting of hydrogen and lower alkyl, each B and B' linking group is independently selected from the group consisting of carbonyl, sulfonyl, amide, and carboxyl;
n and m are independently one or zero;
$R^8$ is a divalent radical selected from the group consisting of an aliphatic group, an alicyclic group, an aromatic group, and a heterocyclic group.

12. A composition of claim 11 wherein $R^8$ has from 5 to about 50 carbon atoms and is selected from the group consisting of a higher alkylene group, a substituted higher alkylene group, an aryl group, an aralkyl group, and an alkaryl group.

13. A composition of claim 1 wherein $R^4$ has the formula:

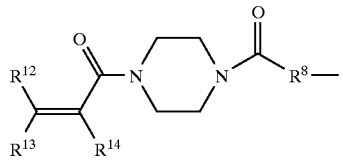

wherein $R^8$ is a divalent group selected from the group consisting of a higher alkylene group, a substituted higher alkylene group, an aromatic group, and a substituted aromatic group, and $R^{12}$, $R^{13}$, and $R^{14}$ are independently selected from the group consisting of hydrogen and lower alkyl.

14. A composition of claim 13 wherein $R^{12}$, $R^{13}$, and $R^{14}$ are hydrogen and $R^8$ is an alkylene radical selected from the group consisting of unsubstituted, straight chain alkylene radicals and alkylene radicals derived from dimer acids.

15. A composition of claim 1 wherein $R^4$ is an alkylene-amido group having the structure —$R^8$—C(O)—N($R^9$)—$R^{10}$, wherein $R^8$ is a divalent group selected from the group consisting of a higher alkylene group, a substituted higher alkylene group, an aromatic group, and a substituted aromatic group, and $R^9$ and $R^{10}$ are independently selected from the group consisting of an aliphatic group, an alicyclic group, an aromatic group, and a heterocyclic group, provided that $R^9$ and $R^{10}$ may together form a divalent alicyclic or heterocyclic radical.

16. A composition of claim 15 wherein $R^9$ and $R^{10}$ are selected from the group consisting of an alkyl group, a substituted alkyl group, an alkenyl group, a substituted alkenyl group, an aromatic group, and a substituted aromatic group.

17. A composition of claim 15 wherein $R^9$ and $R^{10}$ together form a divalent alicyclic or heterocyclic radical.

18. A composition of claim 15 wherein $R^8$ is an alkylene radical selected from the group consisting of unsubstituted, straight chain alkylene radicals and alkylene radicals derived from dimer acids.

19. A composition of claim 1 wherein $R^4$ is an alkylene-ester group having the structure —$R^8$—C(O)—O—$R^{11}$, wherein $R^8$ is a divalent group selected from the group consisting of a higher alkylene group, a substituted higher alkylene group, an aromatic group, and a substituted aromatic group and $R^{11}$ is selected from the group consisting of aliphatic group, an alicyclic group, an aromatic group, and a heterocyclic group.

20. A composition of claim 19 wherein $R^8$ is an alkylene radical selected from the group consisting of unsubstituted, straight chain alkylene radicals and alkylene radicals derived from dimer acids and $R^{11}$ is an alkyl group.

21. A composition of claim 19 wherein $R^8$ is an aromatic group or a substituted aromatic group and $R^{11}$ is an alkyl group.

22. A composition of claim 21 wherein $R^8$ is a phenyl group and $R^{11}$ is an n-butyl group.

23. A polymerizable composition comprising a composition of claim 1 in an amount sufficient to measurably affect a macro-observable physical property of a polymer prepared therefrom, as compared to said polymer prepared without said amount of said polymerizable compound.

24. A polymerizable composition of claim 23 wherein said compound is present in a major amount on a mole percent basis of all of the polymerizable compounds of said composition.

25. A polymerizable composition of claim 23 further comprising a photoinitiator susceptible to ultra-violet radiation.

26. A polymerizable composition of claim 23 wherein said composition is essentially free of acrylate monomers.

27. A process for a stabilizing a composition comprised of a compound of the formula:

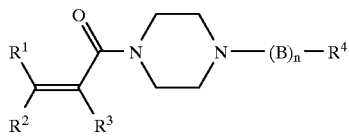

(I)

wherein;
- $R^1$, $R^2$, and $R^3$ are each independently selected from the group consisting of hydrogen and lower alkyl,
- B is a linking group selected from the group consisting of carbonyl, sulfonyl, amide, and carboxyl;
- n is one or zero;
- $R^4$ is a radical selected from the group consisting of a higher aliphatic group, a substituted higher aliphatic group, an alicyclic group, a heterocyclic group, a non-benzenoid aromatic group, said process comprising reducing the amount of unreacted piperazine in the composition to a level that viscosity of the composition does not increase more than 20% when the composition is held at 60° C. for 150 hours when said composition is mixed with a polymerization inhibitor.

28. The composition of claim 1 wherein the viscosity of the composition does not substantially increase when the composition is held at 60° C. for 150 hours.

29. The composition of claim 11 wherein the compound is bis(N'-acrylamido-piperazinyl) dimer acid amide.

30. The composition of claim 11 wherein the compound is bis(N'-acrylamido-piperazinyl) dodecanedioc acid amide.

31. The composition of claim 11 wherein the compound is bis(N'acrylamido piperazinyl) adipic acid amide.

32. A composition having improved stability against gelation comprising a compound of the formula;

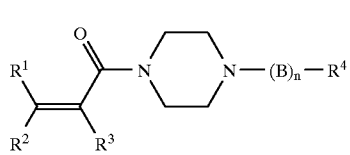

(I)

wherein:
- $R^1$, $R^2$, and $R^3$ are each independently selected from the group consisting of hydrogen and lower alkyl,
- B is a linking group selected from the group consisting of carbonyl, sulfonyl, amide, and carboxyl;
- n is one or zero;
- $R^4$ is a radical selected from the group consisting of a higher aliphatic group, a substituted higher aliphatic group, an alicyclic group, a heterocyclic group, a non-benzenoid aromatic group, and a substituted aromatic group, wherein viscosity of said composition goes not increase more than 100% when the composition is held at 60° C. for 3 hours.

33. The composition of claim 32 wherein the viscosity does not increase more than 100% when the composition is held at 60° C. for more than 150 hours.

34. A method as claimed in claim 27 wherein said polymerization inhibitor is selected from the group consisting of quinones and phenothiazine.

35. A method as claimed in claim 34 wherein said polymerization inhibitor is phenothiazine.

36. The composition of claim 32 wherein the viscosity of said composition does not increase more than 50* when the composition is held at 60° C. for 150 hours.

37. The composition of claim 32 wherein the viscosity of said composition does not increase more than 50* when the composition is held at 60° C. for 3 hours.

38. The composition of claim 32 wherein the viscosity of said composition does not increase more than 20% when the composition is held at 60° C. for 3 hours.

* * * * *